United States Patent
Flohr et al.

(10) Patent No.: US 9,265,471 B2
(45) Date of Patent: Feb. 23, 2016

(54) DETERMINATION OF A MULTI-ENERGY IMAGE

(71) Applicant: SIEMENS AKTIENGESELLSCHAFT, Munich (DE)

(72) Inventors: Thomas Flohr, Uehlfeld (DE); Bernhard Schmidt, Fuerth (DE)

(73) Assignee: SIEMENS AKTIENGESELLSCHAFT, Munich (DE)

( * ) Notice: Subject to any disclaimer, the term of this patent is extended or adjusted under 35 U.S.C. 154(b) by 217 days.

(21) Appl. No.: 14/094,893

(22) Filed: Dec. 3, 2013

(65) Prior Publication Data

US 2014/0161227 A1    Jun. 12, 2014

(30) Foreign Application Priority Data

Dec. 11, 2012   (DE) .......................... 10 2012 222 714

(51) Int. Cl.
*A61B 6/00*   (2006.01)
*A61B 6/03*   (2006.01)

(52) U.S. Cl.
CPC ................. *A61B 6/482* (2013.01); *A61B 6/032* (2013.01); *A61B 6/405* (2013.01); *A61B 6/4035* (2013.01); *A61B 6/481* (2013.01); *A61B 6/504* (2013.01)

(58) Field of Classification Search
CPC ........ A61B 6/482; A61B 6/542; A61B 6/405; A61B 6/4035; A61B 6/488; A61B 6/4241; A61B 6/481; A61B 6/027; A61B 6/06; A61B 6/541; A61B 6/583; A61B 6/469; A61B 6/544; A61B 6/4085; A61B 6/504; A61B 6/4441; A61B 6/0457; A61B 6/032
USPC ........................................ 378/4, 9, 15, 16, 62
See application file for complete search history.

(56) References Cited

U.S. PATENT DOCUMENTS

| | | | |
|---|---|---|---|
| 7,209,537 B2 | 4/2007 | Popescu | |
| 8,199,875 B2 * | 6/2012 | Chandra | ................ A61B 6/032 378/16 |

(Continued)

FOREIGN PATENT DOCUMENTS

| | | |
|---|---|---|
| CN | 1765327 A | 5/2006 |
| CN | 101237819 A | 8/2008 |

(Continued)

OTHER PUBLICATIONS

Chinese Office Action and English translation thereof dated Aug. 27, 2015.

*Primary Examiner* — Irakli Kiknadze
(74) *Attorney, Agent, or Firm* — Harness, Dickey & Pierce, P.L.C.

(57) ABSTRACT

A method is disclosed for determining a multi-energy image via an x-ray device, including an x-ray source and an x-ray detector. The method includes a temporal sequence of individual steps. A first contrast agent-assisted image of an object area is first recorded with a first energy. Then a second contrast agent-assisted image of an object area is recorded with a second energy. A third recording of a third contrast agent-assisted image of the object area is now made with the first energy. By taking the temporal change in the contrast agent signal into account between the first and the third image, a multi-energy image is finally determined by means of the three recordings.

27 Claims, 1 Drawing Sheet

FIG 1

(56) References Cited

U.S. PATENT DOCUMENTS

| | | |
|---|---|---|
| 9,055,919 B2 * | 6/2015 | Proksa ............. A61B 5/4869 |
| 2006/0109951 A1 | 5/2006 | Popescu |
| 2008/0232549 A1 | 9/2008 | Poorter |
| 2008/0253503 A1 | 10/2008 | Proksa |
| 2009/0168950 A1 * | 7/2009 | Jianying ............. A61B 6/032 378/8 |
| 2010/0202675 A1 | 8/2010 | Takanaka et al. |
| 2011/0142194 A1 | 6/2011 | Chandra et al. |
| 2011/0280367 A1 | 11/2011 | Baeumer et al. |
| 2012/0099709 A1 | 4/2012 | Thesen et al. |

FOREIGN PATENT DOCUMENTS

| | | |
|---|---|---|
| CN | 101495040 A | 7/2009 |
| CN | 101797162 A | 8/2010 |
| CN | 102217947 A | 10/2011 |
| CN | 102256548 A | 11/2011 |
| DE | 102004051820 A1 | 5/2006 |
| DE | 102010042683 A1 | 4/2012 |
| JP | 2009297442 A | 12/2009 |
| WO | WO 2011093058 A1 | 8/2011 |
| WO | WO 2012097801 A1 | 7/2012 |

* cited by examiner

DETERMINATION OF A MULTI-ENERGY IMAGE

PRIORITY STATEMENT

The present application hereby claims priority under 35 U.S.C. §119 to German patent application number DE 10 2012 222 714.8 filed Dec. 11, 2012, the entire contents of which are hereby incorporated herein by reference.

FIELD

At least one embodiment of the invention generally relates to a method for determination of a multi-energy image.

BACKGROUND

The properties of x-ray recordings are decisively determined by the spectrum or energy of the x-ray radiation, with which the object to be recorded is irradiated. This is because the capability of various materials in terms of scattering and absorbing x-ray radiation differs as a function of the spectrum or energy of the x-ray radiation.

It is therefore possible, by irradiating an object to be recorded with different spectra or energies of the x-ray radiation, to deduce the material composition of the object to be recorded. The irradiation of an object to be recorded with various spectra or energies of the x-ray radiation is used in particular in medical imaging and is also referred to as a "dual-energy" method. For instance, such a method enables bones or other tissue in the human body to be identified and increases the possibility of evaluating contrast agent-assisted images.

Modern medical devices such as for instance a computed tomography system realize a dual energy method with just one x-ray tube an as x-ray source. In this process use is generally made of so-called "kV-switching", whereby the voltage of the x-ray tube is switched between two values up to several hundred times per second, wherein a voltage value specifies a specific spectrum and/or a specific energy of the x-ray radiation in each instance.

With a tomographic recording, the "kV switching" is embodied such that the voltage changes between the recording of two projections. With "kV switching", in other words during a rotation of the x-ray tube, a plurality of projections at a first voltage and a plurality of projections at a second voltage, is recorded. Since the applied dose also changes with the voltage of the x-ray tube, the current of the x-ray tube and/or the exposure time per x-ray projection is in addition regulated. As a result, modern dual-energy methods are technically challenging.

DE 10 2004 051 820 A1 discloses a method for generating multi-energy images for a tomography device. The tomography device has a recording system for detecting projections of an object area, wherein the recording system includes an x-ray emitter for generating x-ray radiation by means of its voltage, current and exposure time of a predetermined x-ray dose. The voltage between a first voltage value and a second voltage value, which differs therefrom, is set alternately in order to detect high energy projections and low energy projections in each instance.

Furthermore, a further actuating value is set between a first control point assigned to the first voltage value and a second control point assigned to the second voltage value which differs therefrom. In the process the first control point is set as a function of the first voltage value and the second control point is set as a function of the second voltage value such that the respectively generated x-ray radiation has essentially the same x-ray dose.

SUMMARY

At least one embodiment of the invention is directed to determining a multi-energy image in a simple and reliable manner on the basis of contrast agent-assisted recordings by way of an x-ray device having just one individual x-ray source. Furthermore, such a recording should only involve a low dose load for the imaged area.

A method, a computer program product and an x-ray device are disclosed.

An embodiment of the invention is directed to a method for determining a multi-energy image via an x-ray device, including an x-ray source and an x-ray detector. The method includes a temporal sequence of individual steps. A first contrast agent-assisted image of an object area is first recorded with a first energy. Then a second contrast agent-assisted image of an object area is recorded with a second energy. A third recording of a third contrast agent-assisted image of the object area is now made with the first energy. By taking the temporal change in the contrast agent signal into account between the first and the third image, a multi-energy image is finally determined by way of the three recordings. Since the image data is recorded with different energies in the form of sequential recordings of the object area, a "kV switching" is omitted, as a result of which the method can be implemented very easily and reliably. Different contrast agent concentrations at the respective points in time of the various recordings result in artifacts when calculating the multi-energy image without correction. Here such artifacts can be prevented in that the temporal change in the contrast agent signal is taken into account between the two recordings with the first energy. In a particular case of three temporally consecutive recordings, the first and the third image, recorded in each instance with a first energy, are calculated with one another such that a contrast agent signal attuned to the point in time of the second recording can be determined, wherein this contrast agent signal corresponds to a recording with a first energy.

Furthermore, an embodiment of the invention includes a computer program product, which can be loaded directly into a processor of a programmable computer, having program code means, in order to execute the inventive method, if the program product is executed on a computer. This enables the method to be implemented quickly, repeated identically and in a robust manner.

Furthermore, an embodiment of the invention includes an x-ray device, including an x-ray source and an x-ray detector, designed in order to execute the inventive method with the said advantages.

Furthermore, an embodiment of the invention includes an x-ray device, wherein the x-ray source and the x-ray detector can be rotated and moved along a longitudinal axis. As a result, it is particularly simple to record three-dimensional spatial images and to implement an angle-dependent intensity modulation.

BRIEF DESCRIPTION OF THE DRAWINGS

In the figures.

DETAILED DESCRIPTION OF THE EXAMPLE EMBODIMENTS

Figure 1:
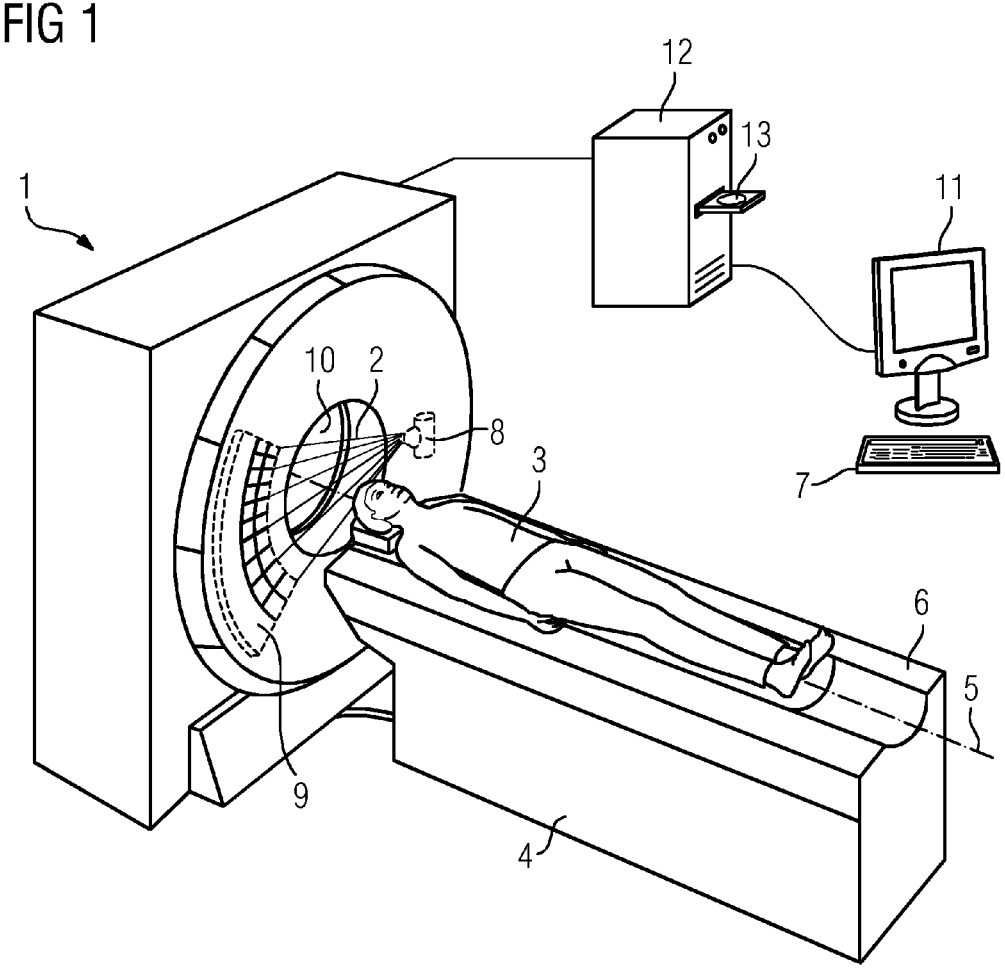
FIG. 1 shows an embodiment of an inventive x-ray device in the form of a computed tomography system.

The present invention will be further described in detail in conjunction with the accompanying drawings and embodiments. It should be understood that the particular embodiments described herein are only used to illustrate the present invention but not to limit the present invention.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

Specific structural and functional details disclosed herein are merely representative for purposes of describing example embodiments of the present invention. This invention may, however, be embodied in many alternate forms and should not be construed as limited to only the embodiments set forth herein.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

Embodiments are described below with reference to an apparatus and also with reference to a method. Features, advantages or alternate embodiments mentioned here are likewise also to be transferred to the other claimed subject matters and vice versa. In other words, the objective claims, which focus on an apparatus for instance, can also be embodied with the features which are described or claimed in conjunction with a method. The corresponding functional features of the method are embodied here by corresponding objective modules.

Recording using a specific energy is understood within the meaning of the application to mean that the spectrum of the x-ray radiation is shifted toward the respective energy. A recording with "low energy" therefore means that it is highly probable that the photons of the x-ray radiation emitted for recording purposes have a lower energy than when recorded with a "high energy". A higher voltage of an x-ray tube thus results in higher energy of the x-ray radiation for instance.

Within the meaning of the present application, a recording can be understood to mean both the recording of an individual x-ray projection and also the recording of an x-ray image, which has been reconstructed from a number of x-ray projections. An image is understood below to mean an x-ray image in the form of an x-ray image reconstructed from individual x-ray projections. In this way in particular, an image may involve three-dimensional spatial images and also sectional images. The recording of an image therefore includes the recording of a number of x-ray projections.

A multi-energy image is an x-ray image which has been reconstructed from projections, which have been recorded with different spectra or energies of the x-ray radiation. Therefore a multi-energy image may also be an image which has been determined with the aid of two images, wherein the two images have each been recorded with different spectra or energies of the x-ray radiation.

A first (or second or third) image is furthermore understood below to mean that this image is firstly (or secondly or thirdly) recorded within a temporal sequence of recordings of images. This applies analogously to a first (or second or third) recording. Accordingly, the point in time of the recording of a first image is before the point in time of the recording of a second image, and the point in time of the recording of a second image is in turn before the point in time of the recording of a third image. It further applies that a finite period of time is meant with a point in time. Within the context of the present application, a point in time includes the periods of time typical of the recording of an image, said periods of time lying in the range of milliseconds to seconds.

An embodiment of the invention is directed to a method for determining a multi-energy image via an x-ray device, including an x-ray source and an x-ray detector. The method includes a temporal sequence of individual steps. A first contrast agent-assisted image of an object area is first recorded with a first energy. Then a second contrast agent-assisted image of an object area is recorded with a second energy. A third recording of a third contrast agent-assisted image of the object area is now made with the first energy. By taking the temporal change in the contrast agent signal into account between the first and the third image, a multi-energy image is finally determined by means of the three recordings. Since the image data is recorded with different energies in the form of sequential recordings of the object area, a "kV switching" is omitted, as a result of which the method can be implemented very easily and reliably. Different contrast agent concentrations at the respective points in time of the various recordings result in artifacts when calculating the multi-energy image without correction. Here such artifacts can be prevented in that the temporal change in the contrast agent signal is taken into account between the two recordings with the first energy. In a particular case of three temporally consecutive recordings, the first and the third image, recorded in each instance with a first energy, are calculated with one another such that a contrast agent signal attuned to the point in time of the second recording can be determined, wherein this contrast agent signal corresponds to a recording with a first energy.

A further aspect of an embodiment of the inventive method includes that the x-ray source is an x-ray tube and that the first and the second energy are set by the voltage of the x-ray tube. The x-ray spectra and/or the energy of the x-ray radiation emitted by the x-ray tube can be particularly easily established by the voltage of the x-ray tube, since it provides a direct relationship between the voltage of an x-ray tube and the energy of the x-ray radiation emitted thereby.

A further aspect of an embodiment of the inventive method includes the first and the second energy being set by means of a filter, so that the energy for a recording can be set particularly easily. A filter then regulates the energy of the x-ray radiation by way of absorption, so that no regulation or only a particularly simple-to-execute regulation of the x-ray tube is required.

A further aspect of an embodiment of the inventive method includes together the first and third recording together having the same applied dose as the second recording. The quality of the image information with the two energies is as a result so widely comparable, that a further image processing can be executed in a particularly simple and robust manner. The quality of the image information may involve in particular the signal-to-noise ratio or the spatial resolution.

A further aspect of an embodiment of the inventive method includes the temporal distance between the first and the second recording and between the second and the third recording being the same.

A further aspect of an embodiment of the inventive method includes the determination of the multi-energy image including an averaging of the first and the third image. The averaging of the first and the third image then results in an image which corresponds to the temporal center point between the point in time of the recording of the first and the third image. The averaged image and the second image are thus comparable in this respect, such that the contrast agent signal corresponds in each instance to a recording at the same point in time.

A further aspect of an embodiment of the inventive method includes the reconstruction of the multi-energy image including a registration of the three images with one another, as a result of which a movement of the object area and/or of the recording object can be compensated for between or during the individual recordings.

A further aspect of an embodiment of the inventive method includes, during the recordings of the images, the intensity of the x-ray radiation being modulated in accordance with the x-ray absorption properties of the recording object. Such a modulation is also known as dose modulation. As a result, the inventive method is particularly efficient, since the intensity which is needed to achieve a certain quality of an x-ray projection is always applied.

Furthermore, an embodiment of the inventive method includes the three images and the multi-energy image involving in each instance three-dimensional spatial images reconstructed from individual x-ray projections. As a result, the cited advantages of the inventive method can also be transferred to three-dimensional spatial images. This is particularly important to medical diagnostics.

Furthermore, an embodiment of the inventive method includes the first energy being lower than the second energy.

Furthermore, an embodiment of the invention includes a computer program product, which can be loaded directly into a processor of a programmable computer, having program code means, in order to execute the inventive method, if the program product is executed on a computer. This enables the method to be implemented quickly, repeated identically and in a robust manner.

Furthermore, an embodiment of the invention includes an x-ray device, including an x-ray source and an x-ray detector, designed in order to execute the inventive method with the said advantages.

Furthermore, an embodiment of the invention includes an x-ray device, wherein the x-ray source and the x-ray detector can be rotated and moved along a longitudinal axis. As a result, it is particularly simple to record three-dimensional spatial images and to implement an angle-dependent intensity modulation.

FIG. 1 shows an embodiment of an inventive x-ray device 1 in the form of a computed tomography system. The inventive x-ray device 1 is for instance also a C-arm device for rotation angiography. The computed tomography system shown here has a recording unit, including an x-ray emitter 8 and an x-ray detector 9. The recording unit rotates during a recording about a longitudinal axis 5, and the x-ray emitter 8 emits an x-ray fan 2 during the recording. The x-ray emitter 8 is an x-ray tube in the example shown here. In the example shown here, the x-ray detector 9 is an array detector with a number of lines. The x-ray detector 9 may also be embodied as a flat panel detector. The x-ray detector 9 is usually embodied as a scintillator counter, in which the high energy x-ray photons are converted by means of a scintillator into low energy photons in the optical spectrum and are then detected by means of a photo diode. Alternatively, the x-ray detector 9 can be embodied as a directly converting detector which converts the high energy x-ray photons into an electrical signal current by means of a semiconductor material directly by way of internal photo excitation using the photovoltaic principle.

When an image is recorded, the patient 3, who represents the object to be recorded in the example shown here, lies on a patient couch 6. The patient couch 6 is thus connected to a couch base 4, such that it supports the patient couch 6 with the patient 3. The patient couch 6 is to this end designed to move the patient 3 along a recording direction through the opening 10 in the recording unit. The recording direction is generally provided by the longitudinal axis 5, about which the recording unit rotates during a recording. However, the longitudinal axis 5 can also be tilted opposite to the recording direction, along which the patient 3 is moved during the recording, for instance by the recording unit being embodied as part of a tiltable gantry.

The extent of the x-ray detector 8 along the longitudinal axis 5, which, in the case of a line detector, depends on the number of lines, and the size of the object area to be detected decisively determine the extent of the advance of the patient couch 6 during the recording of an image. With a particularly extensive x-ray detector 8 and an object area which is less extensive in comparison thereto, a recording without advance of the patient couch 6 may be possible. In a medical context, the object area typically involves organs or body regions, in other words for instance blood vessels, the heart, the kidneys or the liver.

The x-rays of the x-ray fan 2 are attenuated during a recording by the object to be recorded and are detected by the x-ray detector 9 so that an x-ray projection of the recorded object area exists respectively. By rotating the recording unit, x-ray projections are recorded from different directions and/or angles, which may be reconstructed to form a highly resolved, three-dimensional spatial image. In this sense, the recording of individual x-ray projections, for instance within the scope of tomographic recording methods, also involves the recording of an image.

The computer 12 is connected to an output unit 11 and to an input unit 7. The output unit 11 is for instance one (or a number of) LCD-plasma or OLED monitor(s). The output onto the output unit 11 includes for instance a graphic user interface for manually inputting patient data and for activating the individual units of the x-ray device 1 and for inputting and selecting recording parameters. The input unit 7 is for instance a keyboard, a mouse, a so-called touchscreen or also a microphone for speech input.

Figure 2:
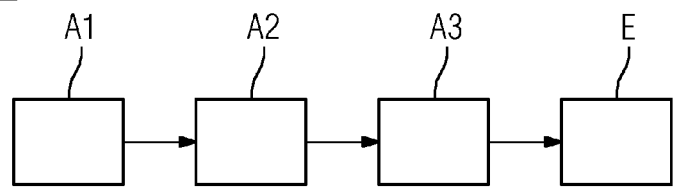
FIG. 2 shows a flow chart of the method according to an embodiment of the invention.

Furthermore, an embodiment of the invention includes a computer program product, which can be loaded directly into a processor of a programmable computer, having program code segments/modules, in order to execute an embodiment of the inventive method described in more detail in FIG. 2, if the program product is executed on a computer. The computer program product is configured such that it can execute an embodiment of the inventive method steps via a computer 12. The computer 12 must in this case have the prerequisites such as for instance a corresponding main memory, a corresponding graphics card or a corresponding logic unit, so that the respective method steps can be executed efficiently. The computer program product is stored for instance on a computer-readable medium 13 or on a network or server, from where can be loaded into the processor of a local computer 12, which is directly connected to the x-ray device 1 or embodied as part of the x-ray device 1.

FIG. 2 shows a flow chart of the method according to an embodiment of the invention. An embodiment of the invention relates to the recording of contrast agent-assisted images. Things which improve the representation of structures and functions of the body during the imaging method are generally defined as a contrast agent. An x-ray image which is recorded without assistance from contrast agents generally does not show any blood vessels. If an iodine-containing solution is injected for instance as contrast agent, the vessels, into which the solution flows, produce x-ray shadows and are therefore visible. Contrast agents are usually distinguished from so-called tracers. This is an artificial, often radioactively marked body's own or foreign substance, which, following introduction into the living body, takes part in the metabolism and furthermore enables or facilitates the most varied of examinations. Within the scope of the present application here, contrast agents are understood to mean both conventional contrast agents and also tracers.

The recording of the same object area with different energies allows conclusions to be drawn as to the material composition of the object area. For instance, different tissue types can be distinguished from one another by means of dual energy methods. This applies in particular during the use of contrast agents. Thus dual energy methods enable the separation of iodine and bones for instance or the identification of plaques in vessels and on the heart. With such methods, the detected signal, for instance in units of Hounsfield (HU), is typically compared during two different recordings with two different energies.

Recordings with different energies can be realized in various ways. Recordings with two x-ray sources 8 and two x-ray detectors 9 are complicated and expensive. The rapid switchover between two energies during a recording, from which two images can then be reconstructed with different energies, is technically very challenging.

With a sequential recording method, the object area is first recorded entirely with one energy and then entirely recorded once again with a second energy. The advantage with a sequential recording method is the technically simple realization. Thus for instance, only an x-ray source 8 and an x-ray detector 9 are required in a sequential recording method with different energies. The problem with conventional sequential recording methods of contrast agent-assisted images with different energies is that the actual contrast agent concentration and thus the contrast agent signal can change between different recordings. As a result, artifacts may arise when determining a multi-energy image. This is particularly relevant if different phases of the contrast agent enrichment are to be observed. It is therefore highly relevant for diagnostic methods that no artifacts exist between two recordings on account of changes to the contrast agent signal.

An embodiment of the invention offers the advantage of sequential recording methods and at the same time avoids its problems. An embodiment of the invention described here particularly easily and reliably allows a contrast agent-assisted multi-energy image to be determined. The method includes a temporal sequence of individual steps. A first contrast agent-assisted image of an object area is firstly recorded with a first energy in step A1. Then, in step A2, a second contrast agent-assisted image of an object area is recorded with a second energy. A third recording of a third contrast agent-assisted image of the object area is now made with the first energy in step A3.

By taking the temporal change in the contrast agent signal into account between the first and the third image, a multi-energy image is finally determined in step E by means of the three recordings. The multi-energy image is for instance a virtual native image. The essential part of the invention is that the temporal change in the contrast agent signal is taken into account between the first and the third recording in that a contrast agent signal is determined, which corresponds to a recording with the first energy at the point in time of the second recording. The determination of the contrast agent signal, which corresponds to a recording with the first energy at the point in time of the second recording, typically takes place in an image-based manner, in other words in HU values. The contrast agent signal is thus known for a specific point in time with two energies. Then current methods can be used to calculate a dual-energy image on the recorded images with the newly determined contrast agent signal.

The recordings are for instance tomography spiral scans, in which a continuous couch advance takes place during the recording of individual x-ray projections of the object area. The recordings may also be tomographic axial scans, with which x-ray projections are recorded at different angles without couch advance. With an axial scan of a large object area, the couch moves between the recording of a set of x-ray projections, wherein a three-dimensional spatial image can be reconstructed from each set of x-ray projections.

In one embodiment of the invention, the x-ray source 8 is an x-ray tube, wherein the first and the second energy are set by the voltage of the x-ray tube. The x-ray spectra and/or the energy of the x-ray radiation emitted by the x-ray tube can be established particularly easily by the voltage of the x-ray tube, since it provides a direct relationship between the voltage of an x-ray tube and the energy of the x-ray radiation emitted thereby. Typical voltage values are 80 kV for a lower energy and 140 kV for a higher energy. Furthermore, the energy can also be set by the current of the x-ray tube.

In one embodiment of the invention, the first and the second energy are set by means of a filter, so that the energy for a recording can be set particularly easily. A filter then regulates the energy of the x-ray radiation via absorption, so that no regulation or only a particularly simple regulation of the x-ray tube to be executed is required. Such a filter is generally attached directly after the exit of the x-ray fan 2 from the x-ray source 8. With a computed tomography system, such a filter with the x-ray source 8 rotates as part of the recording unit.

In an embodiment of the invention, the first and third recording together have the same applied dose as the second recording. Dose is understood within the meaning of the invention to be the energy dose, in other words the energy of the radiation, which an object to be recorded absorbs per kg in weight; for a thus defined dose the unit Gray is used. Since the same object area is irradiated in each instance in the three recordings, the applied dose can be easily regulated by way of the photon flow, in other words the number of photons in a specific energy interval. The photon flow is in turn regulated by way of the intensity of the x-ray radiation and the irradiation duration. The quality of the image information with the two energies is as a result so comparable on account of the same applied dose, that a further image processing can be executed in a particularly simple and robust manner.

In an embodiment of the invention, the first energy is lower than the second energy. Since the dose applied within the scope of the method for the recordings is to be the same in the first and/or second energy, and since the intensity of the x-ray tube is increased with a higher voltage, it is meaningful to divide the dose portion of the lower energy into two recordings. The dose of two recordings with a lower energy can be applied during just one recording with higher energy and with a relatively short recording duration.

In one embodiment of the invention, the temporal distance between the first and the second recording and between the second and the third recording is the same. In this way the temporal change in the contrast agent signal can be taken into account particularly easily, namely by the first and the third image being averaged easily. Then the averaging of the first and the third image results in an image, which corresponds to the temporal center point between the point in time of the recording of the first and the third image. The averaged image and the second image can in this respect be directly comparable, since they each correspond to a recording at the same point in time. In concrete terms, an averaging means that the HU values of two associated image elements, for instance pixels or voxels, are averaged in the first and in the third image. Basically the operation of averaging can also take into account further information, e.g. the HU values of adjacent image elements.

The contrast agent signal, which corresponds to a recording with the first energy at the point in time of the second recording, can also be determined by adjusting the contrast agent signal in the first and the third recording to a function. On account of earlier measurements or with the aid of models, such a function can be selected by developing the contrast agent signal in a specific tissue. This may be an exponential or polynomial function for instance. By way of such an adjustment of already measured contrast agent values to a function, non-linear developments of the contrast agent signal can also be taken into account. A broader area of application is thus available to the invention. The adjustment of the contrast agent signal typically also takes place at the level of individual image elements such as pixels or voxels.

An embodiment of the invention includes a registration of the three recorded images with one another, as a result of which a movement of the object area and/or of the recording object between or during the individual recordings can be compensated for. The registration can take place both rigidly and also non-rigidly. The starting image for a registration can in this case be each of the recorded images, i.e. the first and the second image may for instance each be registered with the third image, or the first and the third image are registered in each instance with the second image. An image, which has emerged from the first and the third image, for instance by way of averaging after registration of the first with the third image, may likewise be registered with the second image.

In a further embodiment of the invention, the intensity of the x-ray radiation is modulated as a function of the x-ray absorption properties of the recording object. Such an intensity or dose modulation takes place in particular during tomographic recordings, since the x-ray absorption properties of the object area change as a function of the irradiation angle. In other words, the same object area with recordings at different irradiation angles can comprise a different degree of x-ray absorption. For instance, the male ribcage of a slim male person generally absorbs more x-ray radiation during a lateral irradiation process than during a dorsal-ventral irradiation process. A higher intensity and/or dose during the recording of a lateral x-ray projection must therefore be applied during the recording of a dorsal-ventral x-ray projection. With a constant image quality, the intensity modulation reduces the applied dose or with a constantly applied dose, the intensity modulation improves the image quality.

What is claimed is:

1. A method for determining a multi-energy image using an x-ray device, including an x-ray source and an x-ray detector, the method comprising:

recording a first contrast agent-assisted image of an object area with a first energy;

recording a second contrast agent-assisted image of the object area with a second energy;

recording a third contrast agent-assisted image of the object area with the first energy; and determining a multi-energy image using the three recordings by taking a temporal change in the contrast agent signal into account between the first and the third image.

2. The method of claim 1, wherein the x-ray source is an x-ray tube and wherein the first and the second energy are set by the voltage of the x-ray tube.

3. The method of claim 2, wherein the first and the second energy are set via a filter.

4. The method of claim 2, wherein the first and third recording together have a same applied dose as the second recording.

5. The method of claim 2, wherein a temporal distance between the first and the second recording and between the second and the third recording is the same.

6. The method of claim 5, wherein the determining of the multi-energy image includes an averaging of the first and the third image.

7. The method of claim 2, wherein the three images and the multi-energy image each respectively involve three-dimensional spatial images reconstructed from individual respective x-ray projections.

8. The method of claim 2, wherein the first energy is less than the second energy.

9. The method of claim 1, wherein the first and the second energy are set via a filter.

10. The method of claim 1, wherein the first and third recording together have a same applied dose as the second recording.

11. The method of claim 1, wherein a temporal distance between the first and the second recording and between the second and the third recording is the same.

12. The method of claim 11, wherein the determining of the multi-energy image includes an averaging of the first and the third image.

13. The method of claim 1, wherein the determining of the multi-energy image includes a registration of the three images with one another.

14. The method of claim 1, wherein, during the recordings, intensity of the x-ray radiation is modulated according to x-ray absorption properties of the recording object.

15. The method of claim 1, wherein the three images and the multi-energy image each respectively involve three-dimensional spatial images reconstructed from individual respective x-ray projections.

16. The method of claim 1, wherein the first energy is less than the second energy.

17. A non-transitory computer readable medium, loadable directly into a processor of a programmable computer, including program code segments useable to execute the method of claim 1 upon being executed on the programmable computer.

18. An x-ray device, comprising:
an x-ray source and an x-ray detector, configured to execute
recording a first contrast agent-assisted image of an object area with a first energy,
recording a second contrast agent-assisted image of the object area with a second energy,
recording a third contrast agent-assisted image of the object area with the first energy, and
determining a multi-energy image using the three recordings by taking a temporal change in the contrast agent signal into account between the first and the third image.

19. The x-ray device of claim 18, wherein the x-ray source and the x-ray detector are rotatable and movable along a longitudinal axis.

20. The x-ray device of claim 18, wherein the first and the second energy are set via a filter.

21. The x-ray device of claim 18, wherein the first and third recording together have a same applied dose as the second recording.

22. The x-ray device of claim 18, wherein a temporal distance between the first and the second recording and between the second and the third recording is the same.

23. The x-ray device of claim 22, wherein the determining of the multi-energy image includes an averaging of the first and the third image.

24. The x-ray device of claim 18, wherein the determining of the multi-energy image includes a registration of the three images with one another.

25. The x-ray device of claim 18, wherein, during the recordings, intensity of the x-ray radiation is modulated according to x-ray absorption properties of the recording object.

26. The x-ray device of claim 18, wherein the three images and the multi-energy image each respectively involve three-dimensional spatial images reconstructed from individual respective x-ray projections.

27. The x-ray device of claim 18, wherein the first energy is less than the second energy.

* * * * *